(12) United States Patent
Zuckermann et al.

(10) Patent No.: US 9,764,953 B2
(45) Date of Patent: Sep. 19, 2017

(54) PEPTOIDS USEFUL FOR THE MINERALIZATION OF APATITE

(71) Applicant: The Regents of the University of California, Oakland, CA (US)

(72) Inventors: Ronald N. Zuckermann, El Cerrito, CA (US); James J. De Yoreo, Clayton, CA (US); Chun-Long Chen, Albany, CA (US); Yung-Ching Chien, Foster City, CA (US); Grayson W. Marshall, Larkspur, CA (US); Sally J. Marshall, Larkspur, CA (US); Kuniko Saeki, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 183 days.

(21) Appl. No.: 14/221,179

(22) Filed: Mar. 20, 2014

(65) Prior Publication Data

US 2015/0174197 A1    Jun. 25, 2015

Related U.S. Application Data

(60) Provisional application No. 61/803,761, filed on Mar. 20, 2013.

(51) Int. Cl.

| | | |
|---|---|---|
| *A61K 38/16* | (2006.01) |
| *C07K 5/10* | (2006.01) |
| *C07K 7/06* | (2006.01) |
| *C07K 7/08* | (2006.01) |
| *C07K 14/00* | (2006.01) |
| *C01B 25/455* | (2006.01) |
| *A61K 33/06* | (2006.01) |
| *A61K 38/10* | (2006.01) |
| *A61K 38/08* | (2006.01) |
| *A61K 38/07* | (2006.01) |
| *A61K 38/06* | (2006.01) |
| *C01B 25/32* | (2006.01) |
| *A61L 27/22* | (2006.01) |
| *A61K 38/00* | (2006.01) |
| *C07K 5/08* | (2006.01) |

(52) U.S. Cl.
CPC .......... *C01B 25/455* (2013.01); *A61L 27/227* (2013.01); *C01B 25/32* (2013.01); *C07K 7/06* (2013.01); *C07K 7/08* (2013.01); *C07K 14/001* (2013.01); *A61K 38/00* (2013.01); *A61L 2430/02* (2013.01); *C07K 5/0827* (2013.01); *C07K 5/1027* (2013.01)

(58) Field of Classification Search
CPC ........ A61K 38/16; A61K 33/42; A61K 33/06; A61K 38/10; A61K 38/08; A61K 38/07; A61K 38/06; C07K 5/08; C07K 5/10; C07K 7/06; C07K 7/08; C07K 14/001; C01B 25/32; C01B 25/455
See application file for complete search history.

(56) References Cited

U.S. PATENT DOCUMENTS

| | | | |
|---|---|---|---|
| 7,736,909 B2 | 6/2010 | Kodadek | |
| 7,834,144 B2 | 11/2010 | Perez et al. | |
| 8,445,632 B2 | 5/2013 | Barron et al. | |
| 8,952,127 B2 | 2/2015 | Chen et al. | |
| 2002/0115612 A1 | 8/2002 | Zuckermann et al. | |
| 2003/0232071 A1* | 12/2003 | Gower .................. | A61L 27/24 424/443 |
| 2004/0161798 A1 | 8/2004 | Kodadek | |
| 2007/0087972 A1 | 4/2007 | Perez et al. | |
| 2007/0116646 A1 | 5/2007 | Klaveness et al. | |
| 2010/0036088 A1 | 2/2010 | Barron et al. | |
| 2011/0300053 A1* | 12/2011 | Chen .................... | C01F 11/183 423/430 |
| 2012/0046443 A1 | 2/2012 | Zuckermann et al. | |

FOREIGN PATENT DOCUMENTS

| | | |
|---|---|---|
| CA | 2714853 | 8/2009 |
| EP | 2252576 | 11/2010 |
| WO | WO 2009/05167 A2 | 8/2009 |
| WO | WO 2010017412 | 2/2010 |

OTHER PUBLICATIONS

Olszta et al Mater. Sci. and Eng. 2007, p. 77.*
Heine et al. Synthesis and screening of peptoid arrays on cellulose membrances. Tetrahedron. 2003, vol. 59, pp. 99919-9930.
Kirshenbaum et. al. Sequence-specific polypeptoids: A diverse family of heteropolymers with stable secondary structure. Proceedings of the National Academy of Science USA, Apr. 1998, vol. 95, 4303-4308.
Wu et al. Structural and Spectroscopic Studies of Peptoid Oligomers . . . Journal of American Chemical Society. Oct. 11, 2003, vol. 125, No. 44, 13525-13530.
Elhadj et al. "Role of molecular change and hydrophilicity in regulating the kinetics of crystal growth," Proc. Natl. Acad. Sci. USA 2006, 103:19237-19242.
Chen et al. "Engineered Biomimetic Polymers as Tunable Agents for Controlling CaCO3 Mineralization," J. Am. Chem. Soc. 2011, 133:5214-5217.
Jee et al., "Oriented hydroxyapatite in turkey tendon mineralized via the polymer-induced liquid-precursor (PILP) process", CrystEngComm, 2011, 13, 2077-2083.

* cited by examiner

*Primary Examiner* — Suzanne Ziska
*Assistant Examiner* — Thurman Wheeler
(74) *Attorney, Agent, or Firm* — Robin C. Chiang; Lawrence Berkeley National Laboratory

(57) ABSTRACT

The present invention provides for a bio-mimetic polymer capable of catalyzing or mineralizing calcium ion and phosphate ions into an apatite.

2 Claims, 20 Drawing Sheets

C792-3

Chemical Formula: $C_{75}H_{93}Cl_6N_{13}O_{30}$; Exact Mass: 1865.4; Molecular Weight: 1869.3

PEPTOIDS USEFUL FOR THE MINERALIZATION OF APATITE

RELATED PATENT APPLICATIONS

This application claims priority to U.S. Provisional Patent Application Ser. No. 61/803,761, filed Mar. 20, 2013, which is hereby incorporated by reference in its entirety.

STATEMENT OF GOVERNMENTAL SUPPORT

The invention described and claimed herein was made in part utilizing funds supplied by the U.S. Department of Energy under Contract No. DE-AC02-05CH11231 and the National Institutes of Health under Grant Nos. R01DE016849-06A1 and R01DE003223-36. The government has certain rights in this invention.

FIELD OF THE INVENTION

This invention relates generally to peptoids.

BACKGROUND OF THE INVENTION

Numerous discoveries within the field of biomimetic research have led to the recognition that proteins can induce or accelerate precipitation of inorganic materials—both crystalline and amorphous—from aqueous precursors under ambient conditions. In vitro experiments have demonstrated that these same proteins as well as shorter chain peptides that mimic certain regions of the proteins can exhibit these same effects absent any biological context. These findings suggest that synthetic molecules might be discovered that can serve as accelerants of crystallization processes in industrial settings. Moreover, design of molecules that mimic the action of these natural biopolymers but that are much more stable against high pressures, temperatures and acidic conditions would result in a technology that is broadly applicable to industrial crystallization. Some example areas of potential application include pharmaceuticals, non-linear optical crystals, scintillators, and materials for sequestration of metals, radionuclides and $CO_2$.

Conservative and minimally invasive dentistry emphasize the reversal of the caries (tooth decay) process and repair of the damaged tissue as a first step to the long term health of the patient. Enamel remineralization is an accepted phenomenon with established mechanisms related mainly to promotion or remineralization aided by fluoride. Dentin remineralization is also believed to occur in some cases but has proven less tractable because of the complex organic-inorganic composite structure based on collagen type I reinforced with apatite that is found in dentin, cementum and bone. Recent approaches to remineralization of the demineralized dentin matrix show promising results, including substantial restoration of the mechanical properties of hydrated carious tissues, a process we have termed functional remineralization (FR) to distinguish it from simple precipitation of mineral that does not lead to such mechanical recovery. Functional remineralization would enhance the minimally invasive trend in dentistry and preserve substantial tooth structure, providing improved oral health care and lower costs.

Currently, many types of materials have been developed as mineralizing or remineralizing agents for enamel and dentin. Fluoride containing products and fluoridated drinking water are important products in this area as one of their functions is to accelerate remineralization of the partially demineralized enamel structure. Briefly, although not completely understood, enamel development occurs by protein guided growth of apatite mineral in the form of enamel rods. During maturation the very long and thin crystallites of the apatite expand as nearly all of the organic matrix that guided the initial formation of the tissue is resorbed. Thus a highly mineralized and cell-free tissue is left as the outer covering of the teeth. When demineralized by the bacterial process known as caries, the mineral is partially dissolved, but if portions of the minerals are left intact, the crystallites can be rebuilt with calcium and phosphate ions from solutions or saliva, and this process can be accelerated by fluoride treatment.

In dentin and bone the fundamental structure of the tissue is different than in enamel, and is based on collagen type I matrix in which mineral reinforces the collagen within the collagen fibrils themselves (intrafibrillar mineral) and between the collagen fibrils (extrafibrillar mineral). In dentin the formative cells or odontoblasts slowly retreat from the dentin-enamel junction and come line the pulp chamber of the tooth. The cells leave tubule pathways in their wake during tissue formation so that the final dentin structure consists of tubules that are partially filled with cellular processes (tails of the cells) separated by intertubular dentin consisting of the mineralized collagen matrix. In addition a highly mineralized cuff forms around the cellular process known as peritubular dentin, but this portion of the structure does not contain collagen. If the initial coating of enamel on the crown or cementum on the root is lost and open tubules are exposed to the oral environment the tooth will become painful due to fluid movement that stimulates nerve endings associated with cells in the pulp chamber. Thus many products for hypersensitive teeth seek to block the open tubules using various approaches to prevent the fluid movement by precipitation of crystals in the tubule lumen.

Dental caries (decay) also may destroy the dentin structure. If the bacterial products penetrate through the enamel and reach the dentin, the dentin structure is subject to demineralization and deproteinization. Demineralization in dentin is more rapid than in enamel for multiple reasons: the apatite crystallites are smaller, contain more carbonate, and there is less mineral since much of the structure is organic matrix. Therefore, current standards of care require that even early dentin lesions must be treated by surgical intervention and restoration. However, there is significant research directed at strategies that aim at remineralization of dentin and most of these are focused on supplying additional calcium and phosphate ions from pastes that release these agents in close proximity to the demineralized area. Newer treatments that show promise now include adjunctive agents that provide the possibility of restoring the mineral within both the intrafibrillar and extrafibrillar compartments of dentin tissue. One such approach is the polymer-induced liquid-precursor (PILP) process that appears to aid the delivery of the ions in the form of nanoclusters to the collagen fibrils and leads to penetration of the collagen and formation of apatite after deposition of amorphous calcium phosphate.

SUMMARY OF THE INVENTION

The present invention provides for a bio-mimetic polymer capable of catalyzing or mineralizing of calcium and phosphate into apatite. In some embodiments, the bio-mimetic polymer is a peptoid or poly-N-substituted glycine. In some embodiments, the peptoid is an amphiphilic polymer. Apatite is a mineral found in calcified tissues in animals such as mammals.

The present invention provides for a method for producing an apatite, comprising: (a) providing a bio-mimetic polymer capable of catalyzing or mineralizing calcium ions and phosphate ions into the apatite, and (b) contacting the bio-mimetic polymer with calcium ions and phosphate ions, such that the apatite is formed.

The present invention provides for a method for treating a tooth or bone in need of such treatment, comprising: (a) administering a bio-mimetic polymer capable of catalyzing or mineralizing calcium ions and phosphate ions into the apatite to a tooth or bone in need of such treatment, and (b) contacting the bio-mimetic polymer with calcium ions and phosphate ions, such that the apatite is formed. In some embodiments, the tooth or bone has a caries lesion The present invention provides for a sequence-specific bio-mimetic polymer (such as a peptoid) that is a catalyst capable of catalyzing, mineralizing, and/or regulating the functional mineralization (including, but not limited to, precipitation) of apatite. This process can be performed under ambient and/or biological conditions. In some embodiments, the apatite formed is precipitated within a lumen of a tubule, such as a dentin tubule, or with a matrix, such as a dentin or collagen matrix.

The present invention provides for peptoid polymers of specific sequence that promotes the formation of apatite, such as precipitate calcium ions and phosphate ions in the form of apatite. The peptoid polymers can modulate the process in aqueous and/or biological conditions with a site/substrate-specific manner. In some embodiments, the peptoid polymers are effective at very dilute concentrations (nano- to micromolar) range. In some embodiments, the peptoids are catalysts, and are re-usable.

BRIEF DESCRIPTION OF THE DRAWINGS

The foregoing aspects and others will be readily appreciated by the skilled artisan from the following description of illustrative embodiments when read in conjunction with the accompanying drawings.

DETAILED DESCRIPTION

Figure 1A:
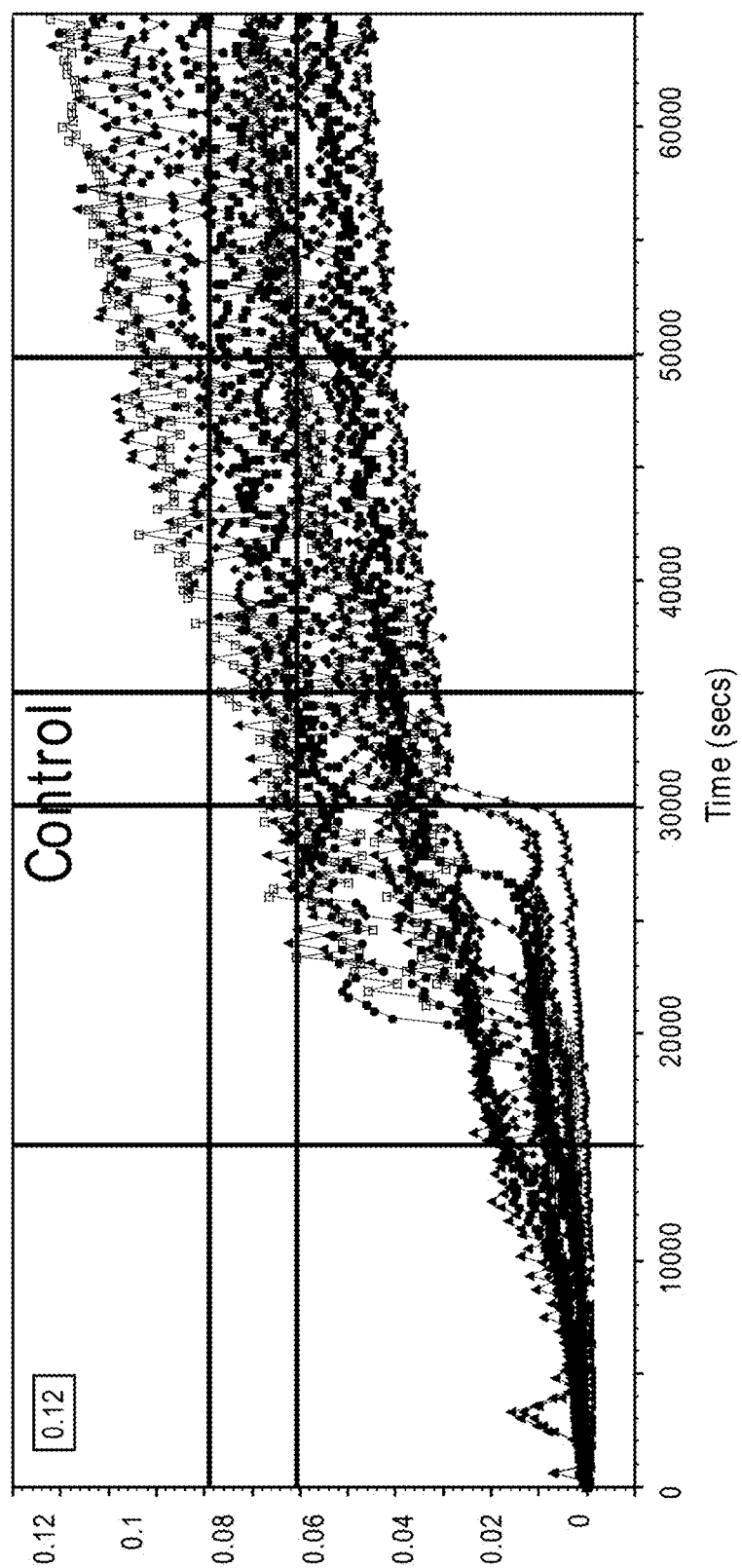
FIGS. 1-A to 1-D show the representative results of turbidity tests to screen out accelerators (e.g., C792-5 (FIG. 1-B)) or inhibitors (e.g., CC81-3 (FIG. 1-C) and CC81-4 (FIG. 1-D)) of CaP mineralization from a library of peptoid molecules. As the nucleation/precipitation of CaP continues (increasing), the absorption of UV light will increase in intensity, as shown the curves in the following diagrams. Multiple red and blue lines (two wave length of UV) represent multiple replicates of samples.
Figure 1A:
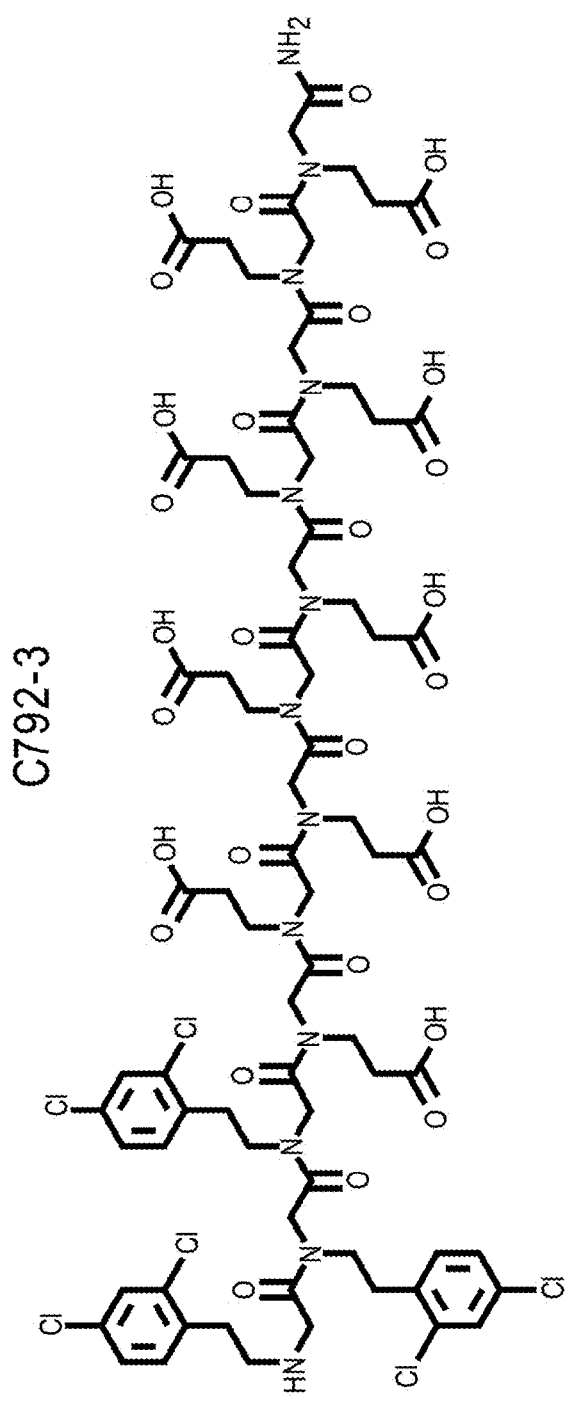
Figure 1A:
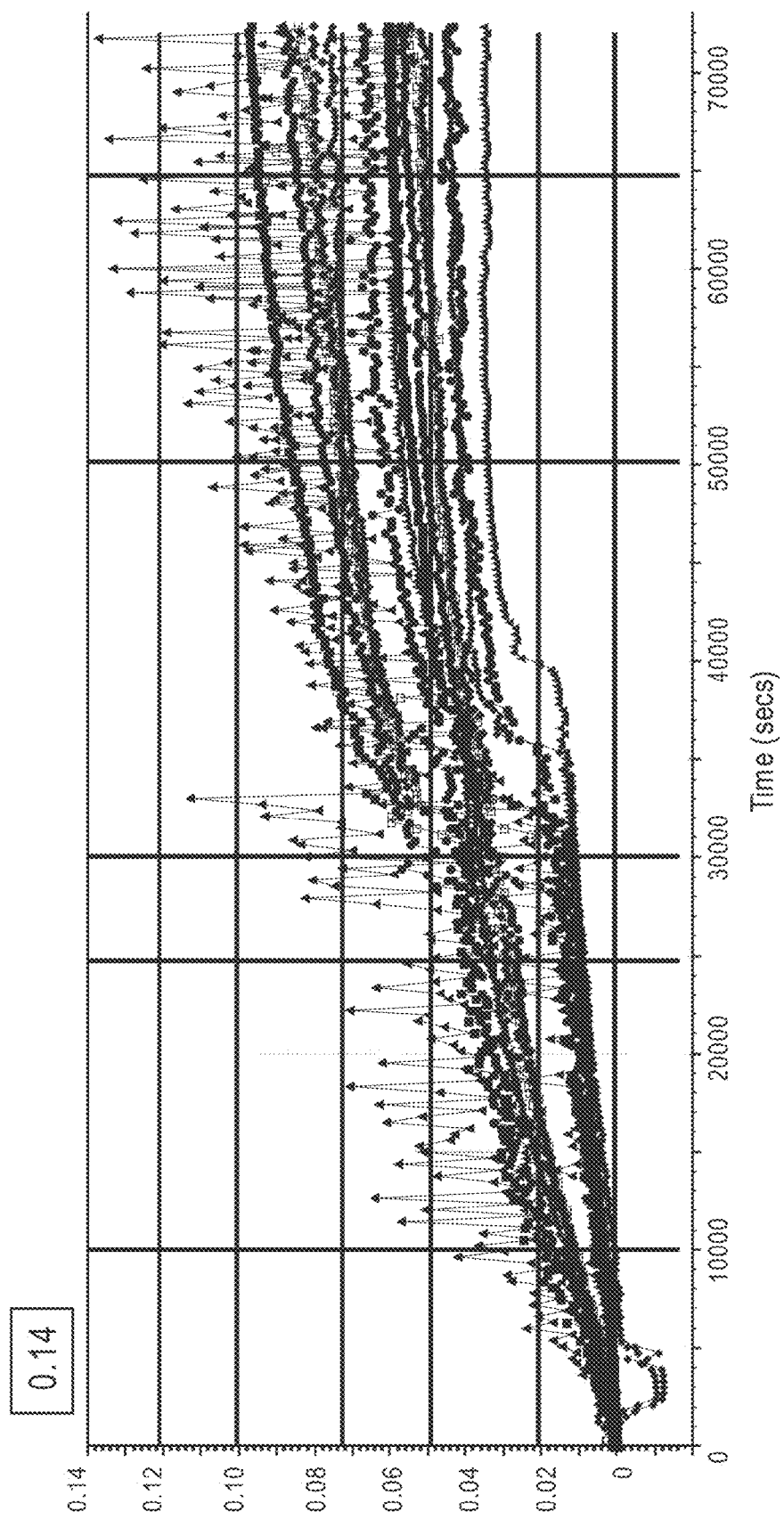
Figure 1B:
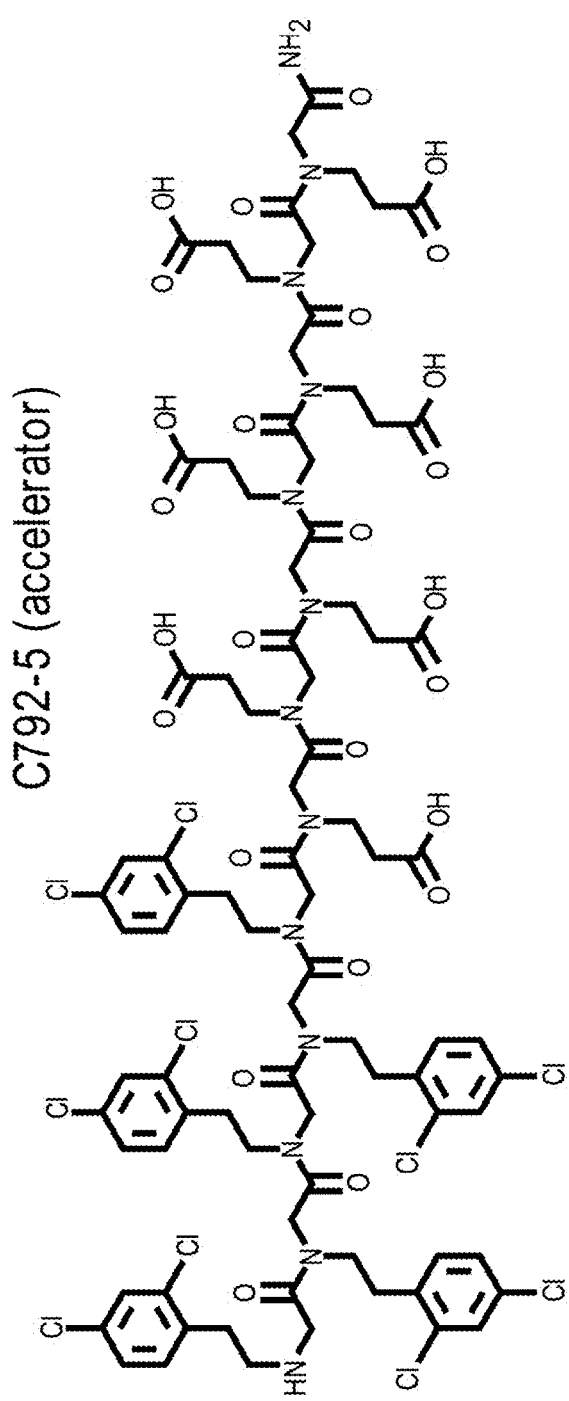
Figure 1B:
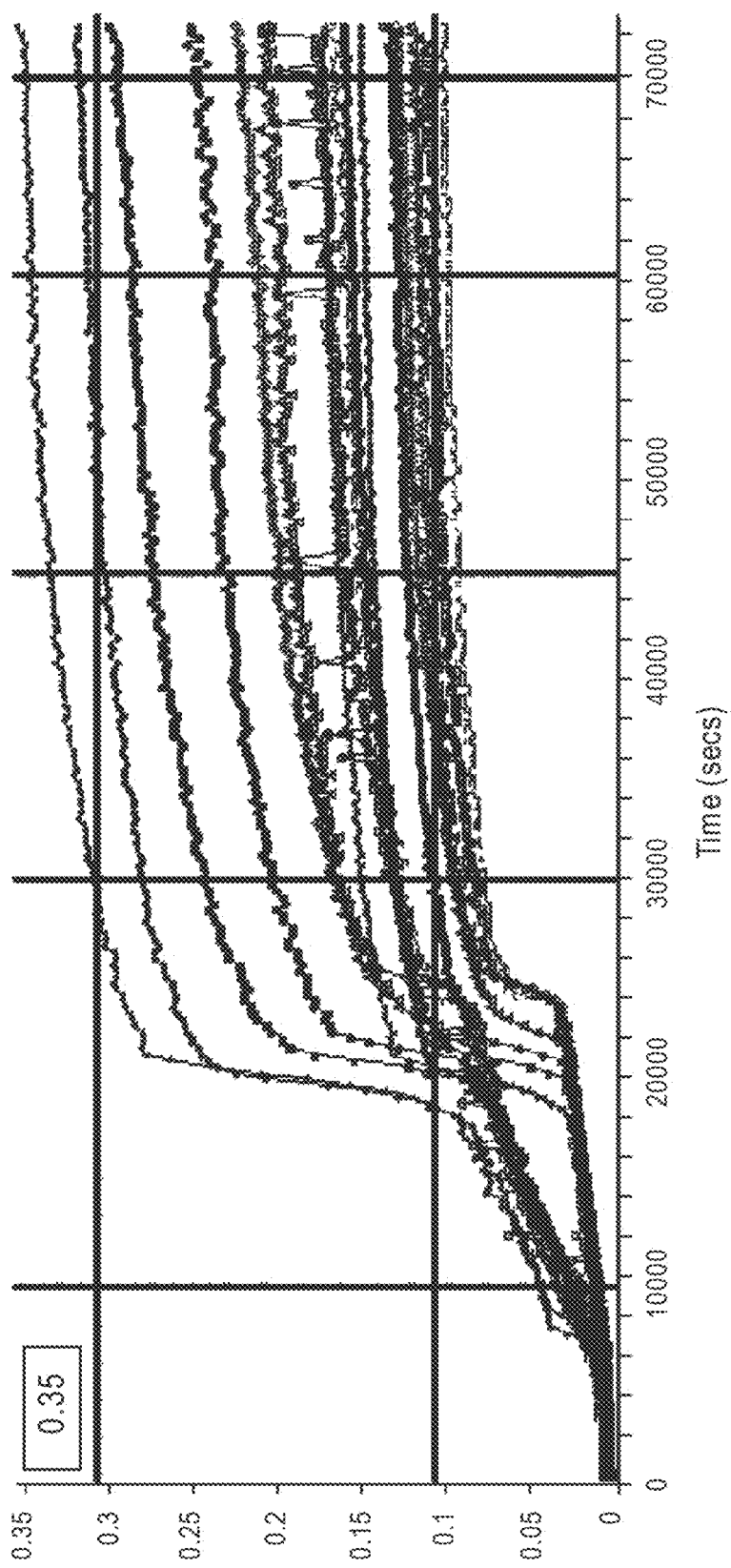
Figure 1C:
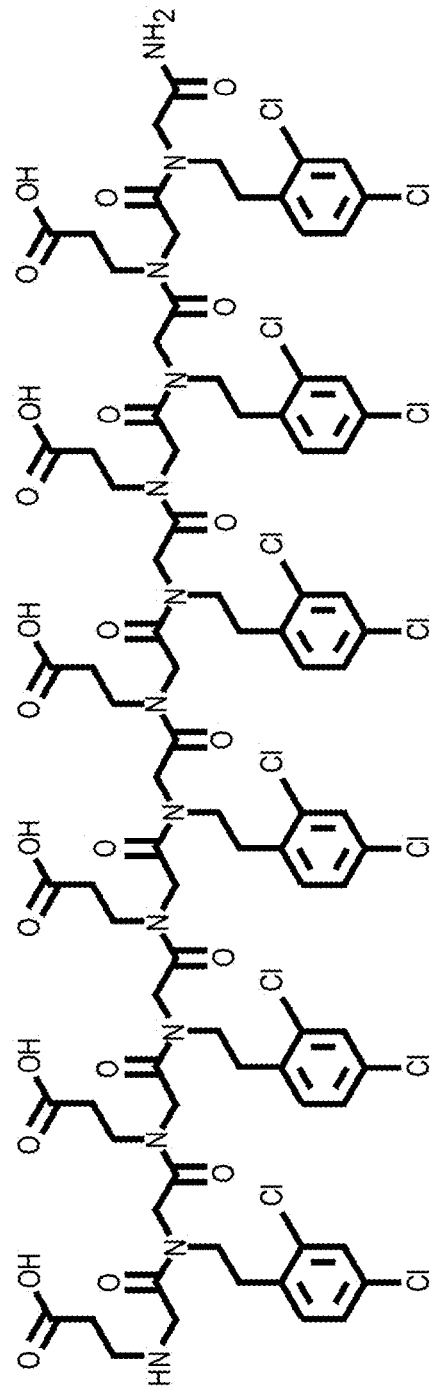
Figure 1C:
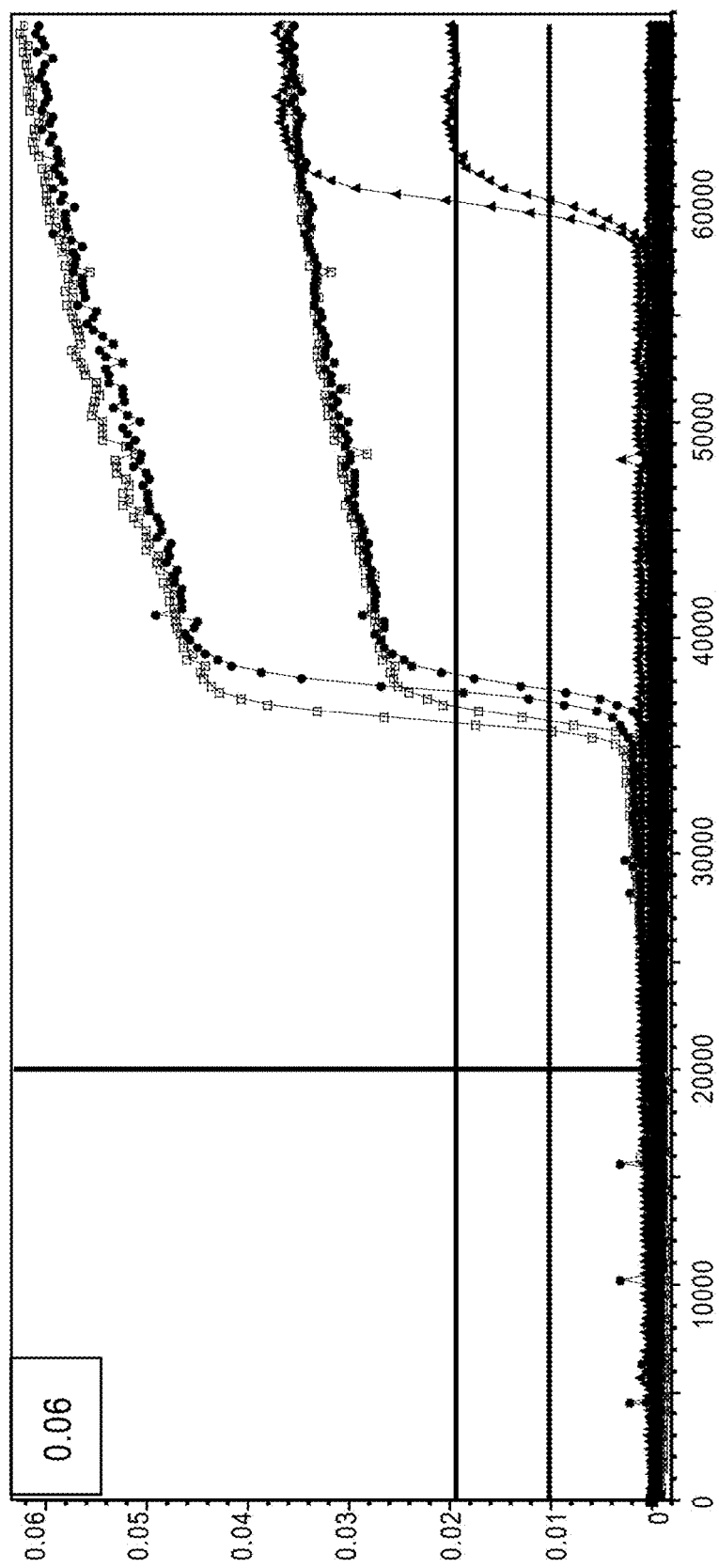
Figure 1D:
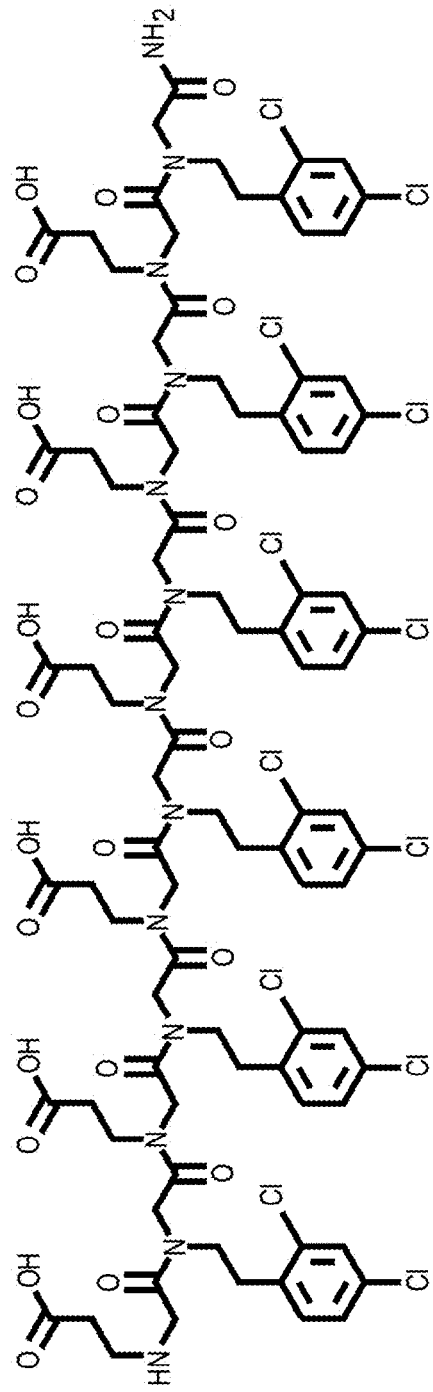
Figure 1D:
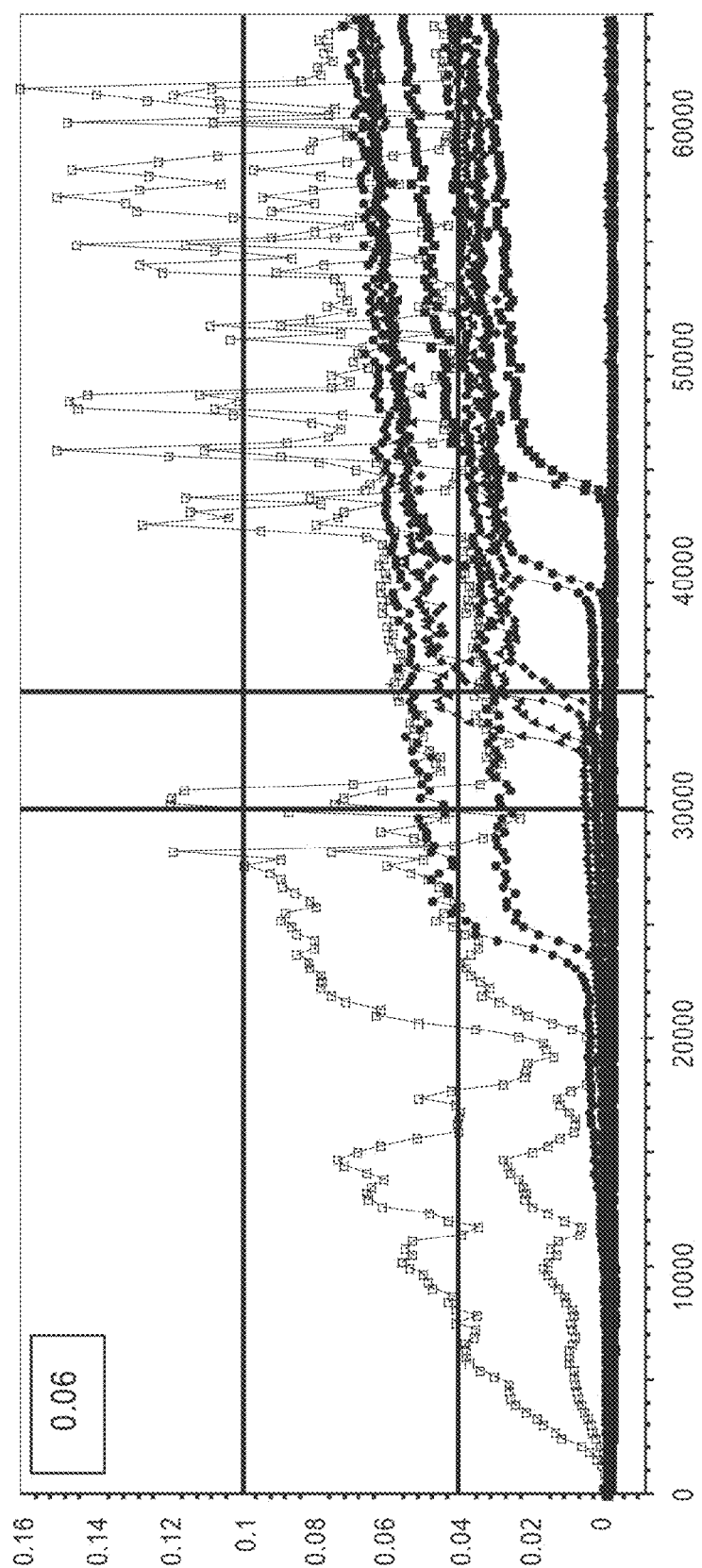

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a peptoid" includes a plurality of such peptoids, and so forth.

In this specification and in the claims that follow, reference will be made to a number of terms that shall be defined to have the following meanings:

The term "peptoid" refers to a peptoid polymer.

In some embodiments, the apatite is hydroxyapatite, fluorapatite, or chlorapatite. In some embodiments, the apatite has the chemical formula: $Ca_5(PO_4)_3(OH)$, $Ca_5(PO_4)_3(F)$, or $Ca_5(PO_4)_3(Cl)$. In some embodiments, the apatite is biological apatite, which is calcium deficient and carbonate rich.

The present invention provides a method for remineralizing a tooth, bone, or artificial tooth or bone composite, comprising: (a) providing a bio-mimetic polymer capable of catalyzing calcium and phosphate ions into apatite, and (b) the bio-mimetic polymer is capable of interacting and binding with a collagen matrix and/or apatite crystals, such that the carious tissues can functionally regrow and restore to their normal mechanical properties. This carious tissues remineralization process can be performed under biological and near-physiological conditions and the remineralized tissues are expected to restore their mechanical properties. In some embodiments, the tooth or bone is affected by a disease that erodes the tooth or bone, such as caries, such as dental caries.

The present invention provides for a sequence-specific bio-mimetic polymer (such as a peptoid) that is a catalyst capable of catalyzing and/or regulating the mineralization of apatite. The sequence-specific peptoid can guide and regulate apatite mineralization in a site-specific, temporal controlled, and pattern-specific manner, which acts as a) an inhibitor that chelates ions (such as cations) and prevent spontaneous precipitation in solution; b) an ion carriers that lead to apatite mineralization onto collagen matrix of dentin, or on the lesion surface of enamel caries; c) a nucleator that initiates nucleation of apatite mineral at the time point of arrival at organic matrix sites with low interfacial energy, and whilst attaining sufficient supersaturation; d) a regulator that modulates the size and shape of apatite crystallites, and delineate their location and orientation.

The present invention provides for peptoid polymers of specific sequence that can interact with both organic matrix (such as collagen matrix) and mineral (such as apatite). The peptoid polymers may prevent collagen degradation via a) binding to collagen matrix and blocking the protease cleavage sites on collagen fibrils, or b) blocking or inactivate protease by direct binding to protease or chelating the cations that are essential to activate protease. Furthermore, the peptoid polymers are effective at very dilute concentrations (nanomolar) range. In some embodiments, the peptoids are catalysts and are re-usable.

In some embodiments, the apatite mineral formed is an apatite crystal. In some embodiments, the apatite crystal has a plate-like crystal habit. In some embodiments, the apatite crystal has an orientation that its c-axis uniaxially co-aligns with the long axis of collagen fibrils and the c-axis of the adjoining crystals. In some embodiments, the apatite crystals bind and co-aligned together via peptoids, developing as lamination structure.

Living organisms strategically harden their specific connective tissues through a well-controlled biomineralization process to produce forceful teeth and skeleton for routine life functions (e.g. feeding, physical and mechanical support, movement, protection, storage, etc.), in which proteins are pivotal in the control of mineral nucleation and growth. Proteins associated with biomineralization of tooth and skeleton are most commonly anionic. The charged groups facilitate them to interact with highly charged mineral crystal surfaces. However, natural proteins or peptides are susceptible to modulations by enzymes (kinases, phosphatases, proteinases) and may lose their function due to the changes of their compositions and structures. The N-substituted glycine peptoids have been shown to exhibit great stability and resist to the modification by some common enzymes. The stability against enzymes and reservation of functionality give the N-substituted glycine peptoids excellence in important pharmaceutical properties (absorption, distribution, metabolism, and excretion, i.e. ADME, as well as safety and efficacy). In this invention, we designed and synthesized a suite of peptoids and screened them for control over calcium phosphates or apatite mineralization in tooth lesions. Our results demonstrated that peptoids exhibited a high degree of control in apatite morphology, crystallinity and orientation within remineralized tissues. For example, an amphiphilic polypeptoid, within nano- to micromolar ranges of concentration, enables the regrowth of peritubular dentin comprising lamellae of well-crystalline apatite crystals.

In some embodiments, the bio-mimetic polymer is a peptoid or poly-N-substituted glycine. In some embodiments, the peptoid is an amphiphilic polymer.

In some embodiments, the peptoid is an inhibitory peptoid in that it alone cannot induce intrafibrillar mineralization in a matrix, such as a dentin lesion matrix. Such inhibitory peptoids in combination with a polyanionic polymer enhance the remineralization apatite, such as of a dentin lesion. Such inhibitory peptoids are CC81-3 and CC81-4.

In some embodiments, the peptoid is peptoid C77-2, C792-3, C792-5, CC81-3, CC81-4, C72-2, C27-1, CC77-7, CC74-2, CC73-1, C77-1, C77-2, or C77-3 (FIGS. 8-14). In some embodiments, the peptoid has a molecular weight from about 1500 g/mol to about 2500 g/mol. In some embodiments, the peptoid has a molecular weight from about 1550 g/mol to about 2200 g/mol. In some embodiments, the peptoid is an oligomeric amphiphilic peptoid, such as a 10-mer to 14-mer amphiphilic peptoid, such as a 12-mer amphiphilic peptoid. In some embodiments, the peptoid is capable of accelerating the process of formation of apatite from calcium ions and phosphate ions equal to or more than ten-fold, when compared to the formation of apatite from calcium ions and phosphate ions in the absence of the peptoid. In some embodiments, the peptoid is capable of accelerating the process of formation of apatite from calcium ions and phosphate ions equal to or more than 20-fold. In some embodiments, the peptoid is capable of accelerating the process of formation of apatite from calcium ions and phosphate ions equal to or more than 40-fold.

In some embodiments, the peptoid comprises from about 3 to about 100 monomeric residues. In some embodiments, the peptoid comprises from about 3 to about 20 monomeric residues. In some embodiments, the peptoid comprises from about 6 to about 20 monomeric residues. In some embodiments, the peptoid comprises from about 6 to about 18 monomeric residues. In some embodiments, the peptoid comprises from about 12 to about 16 monomeric residues. In some embodiments, the peptoid comprises hydrophobic and hydrophilic N-substituents. In some embodiments, each monomeric residue of the peptoid comprises a hydrophobic or hydrophilic N-substituent. In some embodiments, the ratio of the number of monomeric residues comprising a hydrophobic N-substituent to the number of monomeric residues comprising a hydrophilic N-substituent is about from 1:4 to 1:1. In some embodiments, the ratio of the number of monomeric residues comprising a hydrophobic N-substituent to the number of monomeric residues comprising a hydrophilic N-substituent is about from 1:3 to 1:1. In some embodiments, the ratio of the number of monomeric residues comprising a hydrophobic N-substituent to the number of monomeric residues comprising a hydrophilic N-substituent is about from 1:2 to 1:1. In some embodiments, the peptoid comprises two or more (such as four or more) hydrophobic N-substituent which are grouped together, i.e., the hydrophobic N-substituents are on consecutive monomeric residues. In some embodiments, the peptoid comprises two or more (such as four or more)

hydrophobic N-substituent which are grouped together in the middle or at one end of the peptoid. In some embodiments, the peptoid comprises two or more hydrophilic N-substituent which are grouped together i.e., the hydrophilic N-substituents are on consecutive monomeric residues. In some embodiments, the peptoid comprises two or more hydrophobic N-substituents grouped together, and two or more hydrophilic N-substituents grouped together. In some embodiments, the peptoid comprises monomeric residues comprising a hydrophilic N-substituent alternating with monomeric residues comprising a hydrophobic N-substituent.

In some embodiments, the hydrophobic N-substituent comprises an aromatic group. In some embodiments, the hydrophobic N-substituent is —$(CH_2)_n$—$C_6H_5$, —$(CH_2)_n$—$C_6H_4X$, —$(CH_2)_n$—$C_6H_3XX'$, or —$(CH_2)_n$—$C_6H_4$—O—$(CH_2)_m$—$CH_3$; wherein (a) n is 1, 2, 3, or 4, (b) m is 1, 2, 3, or 4, (c) X and X' are independently a halogen, such as F, Br, Cl, or I, and (d) the benzene is para-, ortho-, and/or meta-substituted. In some embodiments, the hydrophilic N-substituent comprises a carboxylic acid, sulfate, sulfonate, phosphate, phosphonate group, or the like. In some embodiments, the hydrophilic N-substituent is —$(CH_2)_p$—COOH, wherein p is 1, 2, 3, or 4.

In some embodiments, the peptoid comprises from about 6 to about 18 monomeric residues, and two or more (such as four or more) hydrophobic N-substituents grouped together, and two or more (such as four or more) hydrophilic N-substituents grouped together, wherein each hydrophilic N-substituent comprises a carboxylic acid. In some embodiments, the hydrophilic N-substituent comprises alternate carboxylic acid and phosphonate group to mimic mineral-binding motifs in natural phosphoproteins that regulate biomineralization.

The peptoid of the present invention can be synthesized using the following process: each residue is installed in two steps: acylation and displacement. In the acylation step a haloacetic acid, typically bromoacetic acid activated by diisopropylcarbodiimide reacts with the amine of the previous residue. In the displacement step (a classical $S_N2$ reaction), an amine displaces the halide to form the N-substituted glycine residue. The peptoids can be synthesized or produced using the methods taught in U.S. Provisional Patent Application Ser. Nos. 61/065,189, filed Feb. 8, 2008, and 61/086,773, filed Aug. 6, 2008; U.S. patent application Ser. No. 12/378,034, filed Feb. 9, 2009; U.S. Patent Application Publication Nos. 2011/0300053 and 2012/0046443A1; and, PCT International Patent Application Nos. PCT/US2009/000840, filed Feb. 9, 2009, and PCT/US2009/053037, filed Aug. 6, 2009 (all of which are hereby incorporated by reference).

The present invention provides for a method for producing an apatite, comprising: (a) providing a bio-mimetic polymer capable of catalyzing or mineralizing calcium ions and phosphate ions into the apatite, and (b) contacting the bio-mimetic polymer with calcium ions and phosphate ions, such that the apatite is formed.

The present invention provides for a method for treating a tooth or bone in need of such treatment, comprising: (a) administering a bio-mimetic polymer capable of catalyzing or mineralizing calcium ions and phosphate ions into the apatite to a tooth or bone in need of such treatment, and (b) contacting the bio-mimetic polymer with calcium ions and phosphate ions, such that the apatite is formed. In some embodiments, the tooth or bone has a caries lesion The present invention provides for a sequence-specific bio-mimetic polymer (such as a peptoid) that is a catalyst capable of catalyzing, mineralizing, and/or regulating the functional mineralization (including, but not limited to, precipitation) of apatite. This process can be performed under ambient and/or biological conditions. In some embodiments, the apatite formed is precipitated on or in a tooth, bone, enamel, artificial composite, within a lumen of a tubule, such as a dentin tubule, or within a matrix, such as a dentin or collagen matrix.

Figure 15:
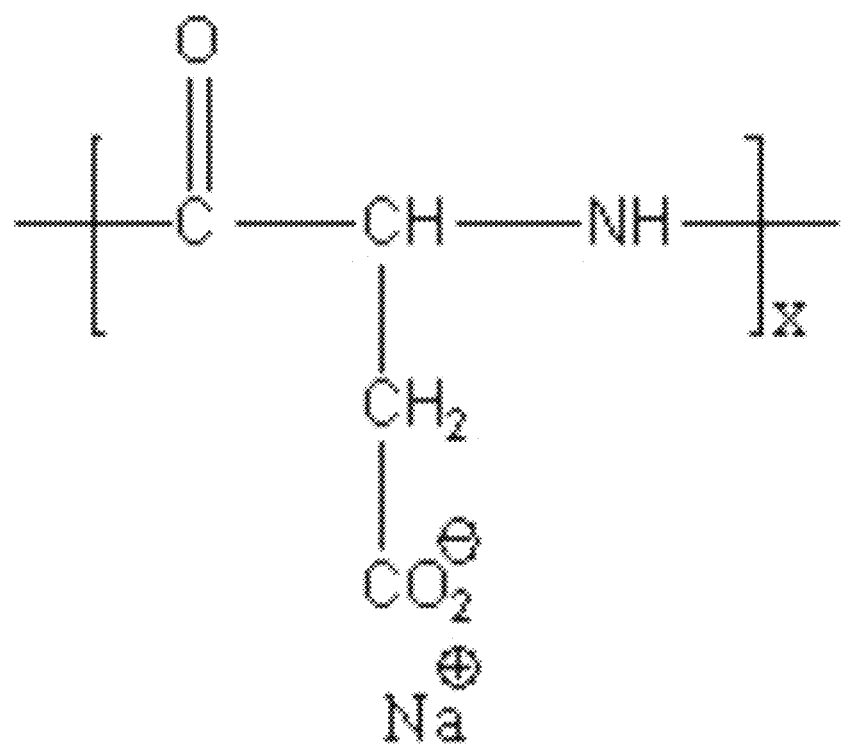
FIG. 15 shows the structure of a polyaspartic acid suitable for the present invention.

In some embodiments, the providing or administering step further comprises providing or administering a polyanionic polymer optionally to the tooth or bone, such as an acidic polypeptide, such as polyaspartic acid. An suitable polyaspartic acid has the formula depicted in FIG. 15. In some embodiments, x is equal to or more than about 10, 20, 50, 100, or 200.

In some embodiments, the tooth, bone or artificial composite is outside of the body of animal when the bio-mimetic polymer and optionally the polyanionic polymer are provided or administered to the tooth, bone or artificial composite. After mineralization has taken place, i.e., apatite formation, the tooth, bone or artificial composite is implanted into the animal, such as a mammal, such as a human.

The present invention provides for peptoid polymers of specific sequence that promotes the formation of apatite, such as precipitate calcium ions and phosphate ions in the form of apatite. The peptoid polymers can modulate the process in aqueous and/or biological conditions with a site/substrate-specific manner. In some embodiments, the peptoid polymers are effective at very dilute concentrations (nano- to micromolar) range. In some embodiments, the peptoids are catalysts, and are re-usable.

Peptoids are a novel class of non-natural polymers recently developed to mimic both structures and functionalities of peptides and proteins, and bridge the gap between biopolymers and bulk polymers. Sequence-specific peptoids can be efficiently synthesized by using automated solid-phase synthesis starting from a large number of chemically diverse amine building blocks. Moreover, peptoids exhibit much higher protease stability and thermal stability than peptides or proteins.

The invention having been described, the following examples are offered to illustrate the subject invention by way of illustration, not by way of limitation.

Example 1

Screening Peptoids for Modulating Calcium Phosphate Mineralization

Peptoids were screened for their effect on calcium phosphate nucleation and growth by turbidity test. The turbidity test is using a microplate reader to measure the absorbance of UV light increasing with the nucleation and growth of calcium phosphate from solutions. Calcium chloride dihydrate was dissolved in Tris buffered saline (TBS, pH=7.4) at a 13.5 mM concentration and peptoid polymers were added to various concentration of micromolar. An equal volume of di-potassium phosphate solution at a 6.3 mM was added to the calcium-polymer mix, resulting in a calcium-to-phosphate ratio of 2.14. The effect of each peptoid was compared to the control run with no addition of polymers (FIG. 1).

Example 2

Biomimetic Peptoid Polymers for Regulating Matrix-Guided Biomineralization

Physiological mineralization of extracellular collagen matrix usually requires cell to direct the process and is achieved with the aids of acidic, anionic non-collagenous proteins. Lately, the biomimetic polymer-induced-liquid-precursor (PILP) process has been proven an effective acellular approach to mineralize a variety of collagen scaffolds. The PILP process was applied to remineralize decalcified tissues, such as dentin lesions, and partially restored the structure and elastic modulus (E) of collagen matrix. Since essential organic components of calcified tissues are very likely removed during the acid dissolution of minerals and compromise the remineralization of remaining collagen matrix in the tissues, we started to design and evaluate peptoids for improving calcified tissues remineralization.

The present invention provides for a family of amphiphilic peptoid polymers that is synthesized using a minimalist monomer set consisting of a hydrophobic monomer N-[2-(X-phenylethyl)]glycine (NXpe) (X=4-H, 4-Cl, 4-OMe, or 2,4-dichloro), and a hydrophilic monomer N-(2-carboxyethyl)glycine (Nce). A small library of peptoids was made by varying the X groups, the number of carboxylic acid residues, the position of the hydrophobic monomers, and the main-chain length (12 or 16 monomers). The amphiphilic characteristics of these peptoid polymers enable their interplay with collagen matrix and minerals via ionic or hydrophobic/hydrophilic interactions, potentially acting as ions carriers, mineral nucleators, or "adhesive" of collagen matrix/minerals or minerals/minerals. Amphiphilic peptoid polymers may complement the anionic polymer used in PILP process, which sequesters calcium and phosphate ion clusters to form CaP precursor droplets, and infiltrates collagen fibrils to grow predominantly intrafibrillar minerals (Sang Soo Jee, Rajendra Kumar Kasinath, Elaine DiMasi, Yi-Yeoun Kim and Laurie Gower, "Oriented hydroxyapatite in turkey tendon mineralized via the polymer-induced liquid-precursor (PILP) process", *Cryst Eng Comm*, 2011, 13, 2077-2083; hereby incorporated by reference).

Figure 2:
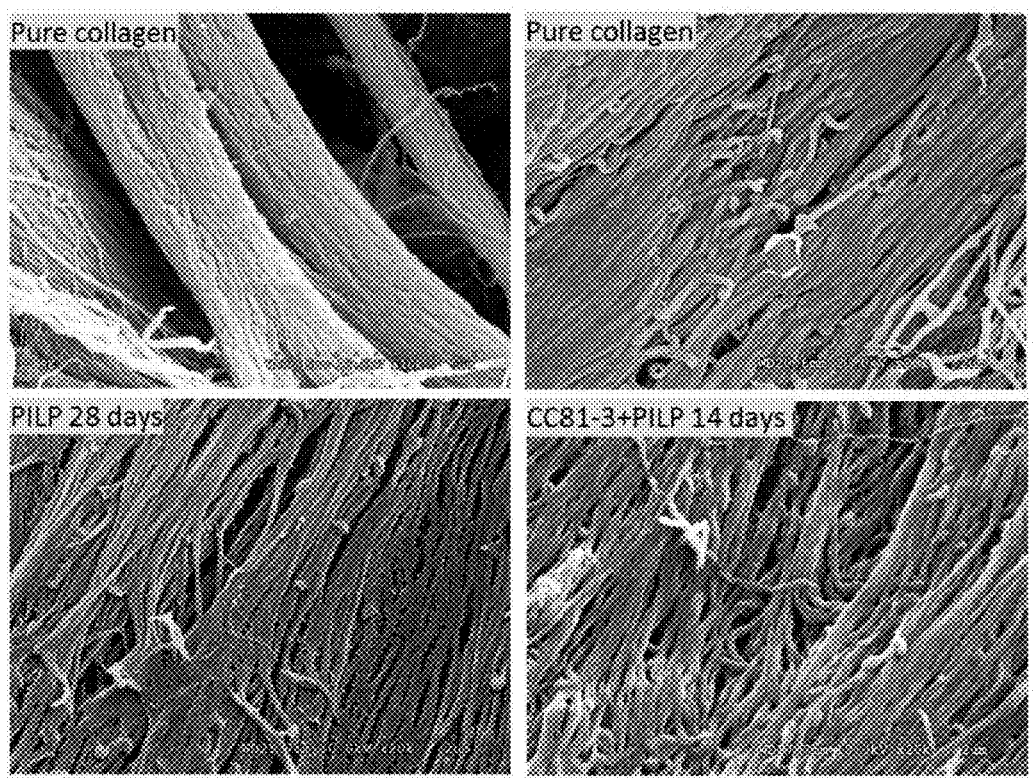
FIG. 2 shows the potentials of peptoid (CC-81-3) enhancing mineralization of collagen matrix. Peptoid aided PILP mineralization process at very dilute concentrations (<2 micromolar) range and attained high degree of mineralization of each collagen fibrils.
Figure 3:
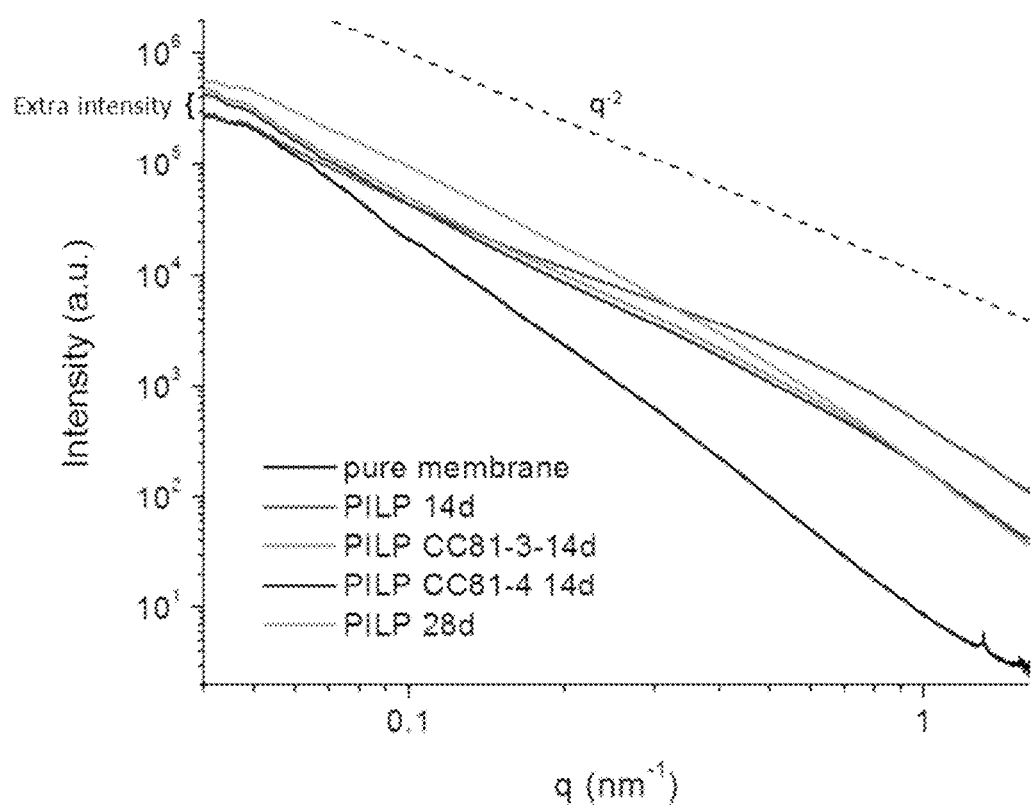
FIG. 3 shows the analysis of small-angle x-ray scattering. Mineralization via PILP process forms disc-like crystals following q-2 line (dashed line) Extra intensity at low q with peptoids.

Several types of collagen matrix were tested with peptoid/PILP or PILP-only process. Peptoid/PILP process can achieve higher degree of mineralization faster than PILP-only process (FIGS. 2 and 3). A bundle of pure type I collagen fibrils display D-banding periodicity under high resolution SEM (FIG. 2), and these D-banding can be obscure and masked when intra- or extra-fibrillar minerals fill in, yielding smooth appearance of collagen fibrils. Within 14 days, peptoid/PILP process can produce highly mineralized collagen fibrils appear smoother (more minerals) than those mineralized by PILP-only process for 28 days (FIG. 2). Small-angle x-ray scattering (SAXS) analyses indicate that both processes produced mostly 'disc-like' crystals, but those formed with peptoid have more polydispersive thickness and larger diameters than PILP-only process (FIG. 3).

Example 3

Biomimetic Peptoid Polymers as Catalytic Agents for Enhancing Mineralization in Dentin Lesion Peptoids either accelerating or inhibiting calcium phosphate nucleation and growth are selected from the turbidity test and experimented for mineralization of human dentin lesions. Human teeth samples are obtained from the UCSF dental hard tissue specimen core according to protocols approved by the UCSF Committee on Human Research. After extraction, the teeth are sterilized with gamma radiation and stored intact in de-ionized water and thymol at 4° C. Dentin blocks measuring 6 mm in length, and 3 mm in width and thickness are cut from the mid-coronal region of the selected teeth perpendicular to the tubule direction. A dentin lesion is artificially prepared from a non-carious human dentin block via exposing a reacting surface (area=9 $mm^2$) to a 0.05M, pH 5 acetate buffer to produce a 140 μm deep lesion.

Acetate buffer produces two distinct zones in 140 μm-deep artificial dentin lesions: an "Outer Zone" (OZ) of 60 μm from the surface with low elastic modulus (E) and a "Graded Zone" (GZ) with increasing E to normal dentin values. Remineralization via a polymer-induced-liquid-precursor (PILP) process partially restores E, with different results within the two zones: the GZ regains full intrafibrillar mineralization, while the OZ recovers 50% of its properties after 28 days. In this study, we evaluated synthetic peptide-like poly-N-substituted glycines (peptoids) for improving dentin remineralization.

(1) 140 μm-deep artificial lesions in non-carious human dentin blocks and 2) demineralized, ~150 μm-thick non-carious dentin discs are produced with 0.05M acetate buffer (pH=5.0), and remineralized using the PILP process with calcium phosphate solution containing 1) 27 KDa poly-L-aspartate, and/or 2) several types of peptoids as precursor inducing agents. Peptoids are screened for their effect on calcium phosphate precipitation by turbidity and dynamic light scattering. Remineralization is conducted at pH=7.4 (37° C.) for 0, 7, or 14 days. Mineral-matrix ultrastructure, mineral orientation and crystallinity are determined by TEM/selected area electron diffraction (SAED). Cross sections are studied using SEM. Mechanical property profiles are obtained by nanoindentation and mineral profiles by micro X-ray computed tomography (MicroXCT™). Demineralized and remineralized dentin discs are analyzed by small angle X-ray scattering (SAXS) and micro-Raman spectroscopy.

Figure 4:
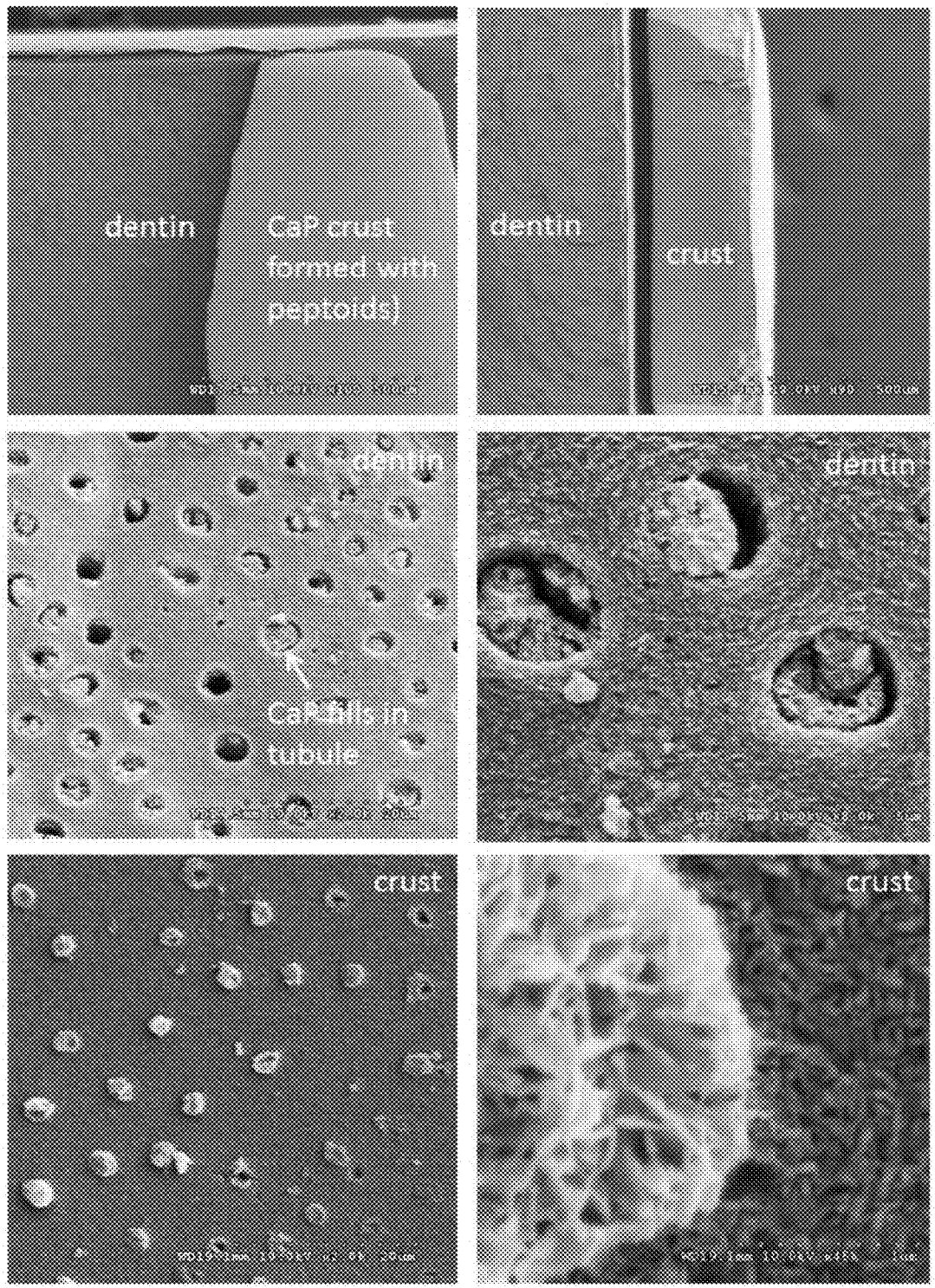
FIG. 4 shows a layer of calcium phosphate crust formed on top of dentin lesions using peptoid polymer only for remineralization.

Peptoids either accelerating or inhibiting calcium phosphate nucleation and growth are introduced in mineralization experiment of human dentin lesions. Peptoid polymers are added at determined micromolar concentration to calcium chloride solution. An equal volume of di-potassium phosphate solution is added to the calcium-polymer mix, resulting in a calcium-to-phosphate ratio of 2.14. Solutions are prepared from reagent grade calcium chloride dihydrate ($CaCl_2.H_2O$), and potassium phosphate di-basic ($K_2HPO_4$) dissolved in Tris buffered saline (TBS, pH=7.4) and filtered to remove insoluble chemicals. Both peptoid types induce uniform calcium phosphate precipitates particularly on top of lesions, but these do not permeate into the lesion matrix (FIG. 4). Dentin tubules are also filled with calcium phosphate precipitates.

Figure 5:
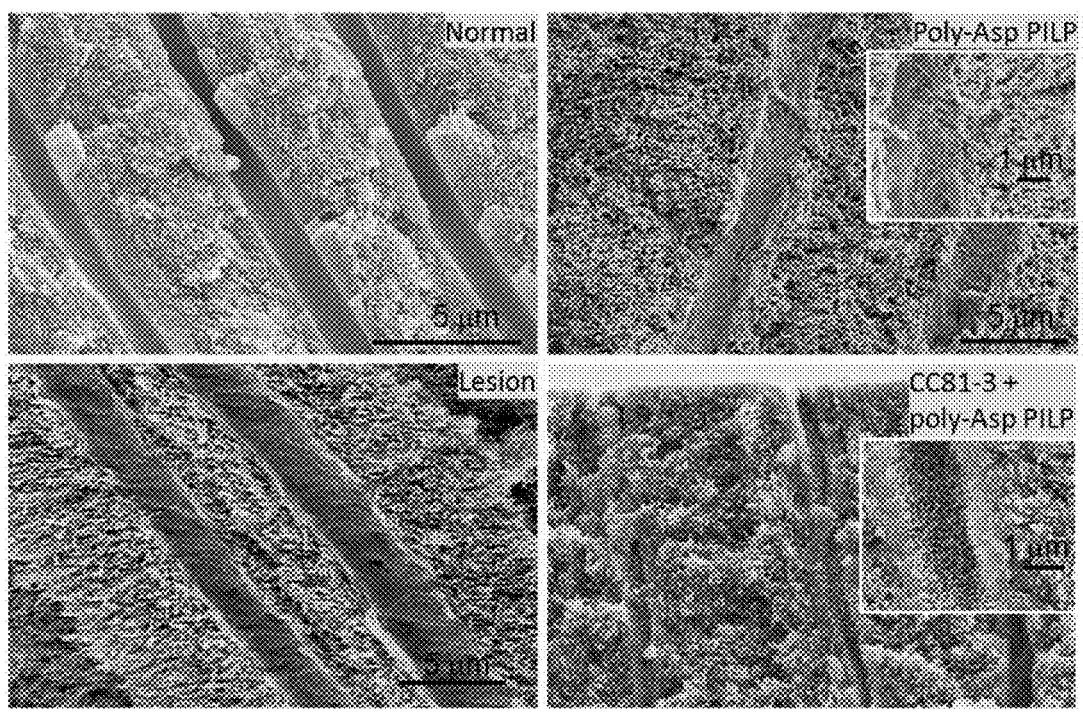
FIG. 5 shows PILP (poly-L-Aspartate alone) induces mainly intrafibrillar mineralization in collagen matrix. Peptoid (CC81-3)/PILP approach enhances intrafibrillar, extra-fibrillar, and even peritubular mineralization so that the remineralized lesion resembles normal dentin.

Peptoids either accelerating or inhibiting calcium phosphate nucleation and growth were tested for remineralization of dentin lesions. Both peptoid types induce uniform calcium phosphate precipitates on top of lesions, but these do not permeate into the lesion matrix. We then combined poly-L-aspartate and peptoids in remineralization experiments. While accelerating peptoids counteract poly-L-aspartate, inhibitory peptoids complement poly-L-aspartate and enhance remineralization of dentin lesions. Dentin remineralization is studied using poly-L-aspartate via a polymer-induced-liquid-precursor (PILP) process, which partially restores the structure and elastic modulus (E) at dentin lesions. Peptoids are evaluated for improving dentin remineralization. Poly-L-aspartate and peptoids are combined in remineralization experiments. Peptoid molecules are introduced either (1) into calcium chloride solution mixing with poly-L-aspartate to initiate remineralization, or (2) via pre-incubation with dentin lesion in solution for various periods of time, then immediately following up with PILP remineralization process for 14 days. The results show that, while accelerating peptoids counteract poly-L-aspartate, inhibitory peptoids complement poly-L-aspartate and enhance remineralization of dentin lesions (FIG. 5).

Figure 6:
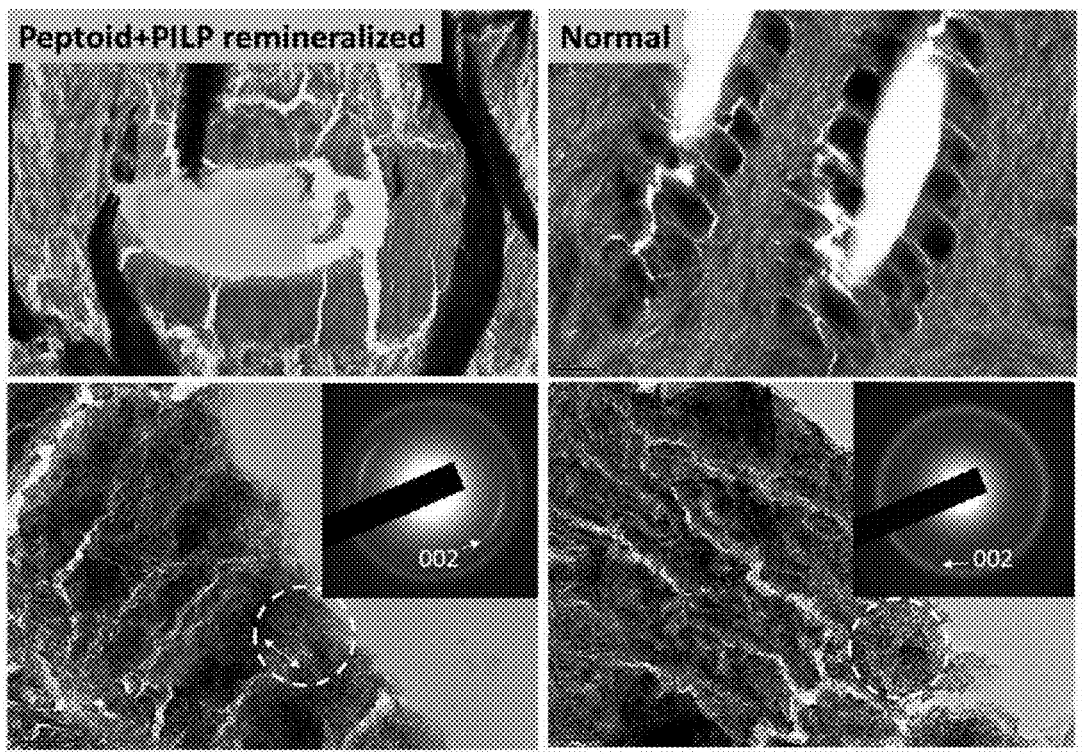
FIG. 6 shows regrowth of peritubular dentin with peptoid (CC81-3) comprise co-aligned, lamellae of hydroxyapatite, distinct from normal peritubular dentin.
Figure 7:
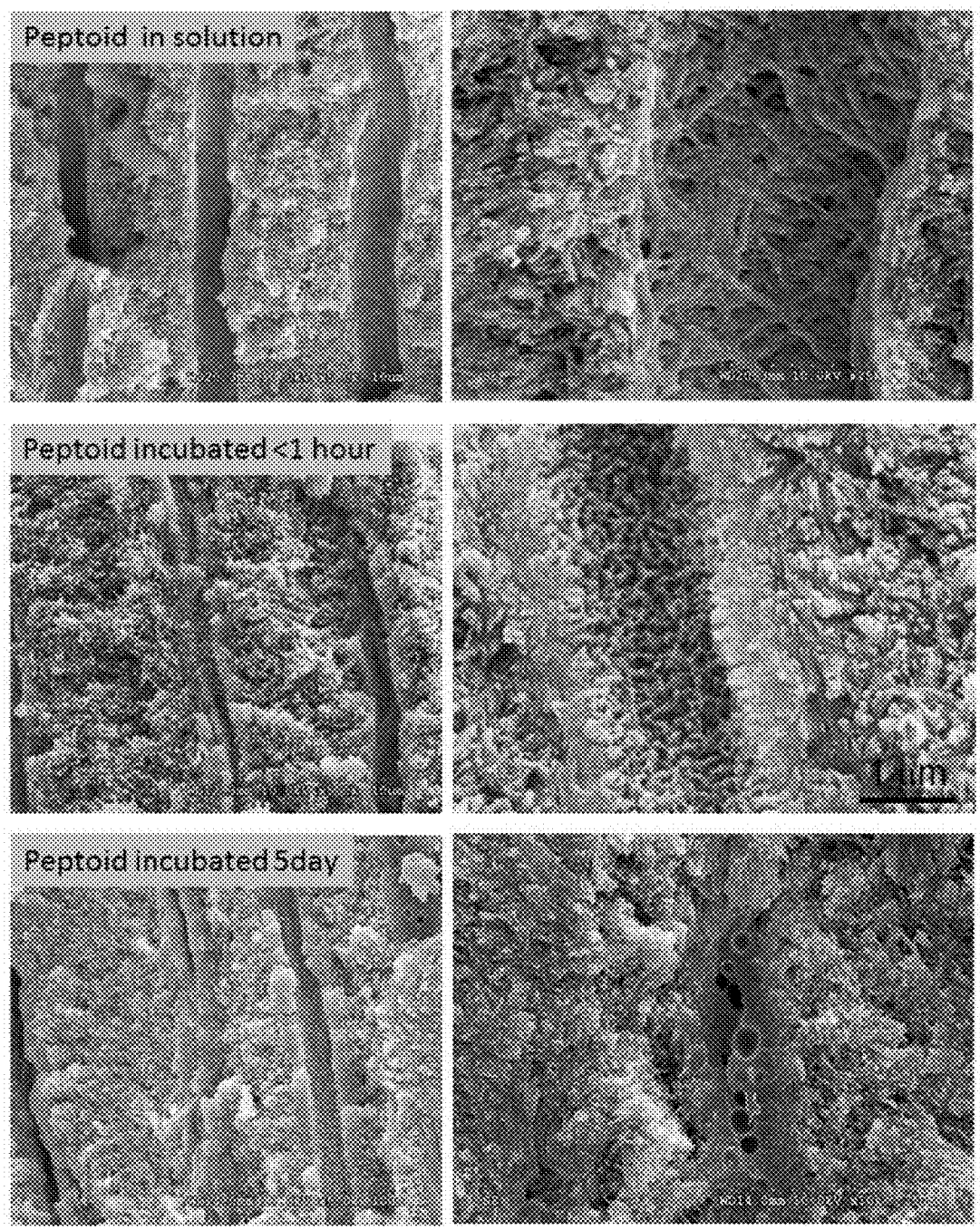
FIG. 7 shows that the longer the peptoid incubation time, the more regrowth in the dentin tubule lumen.
Figure 8:
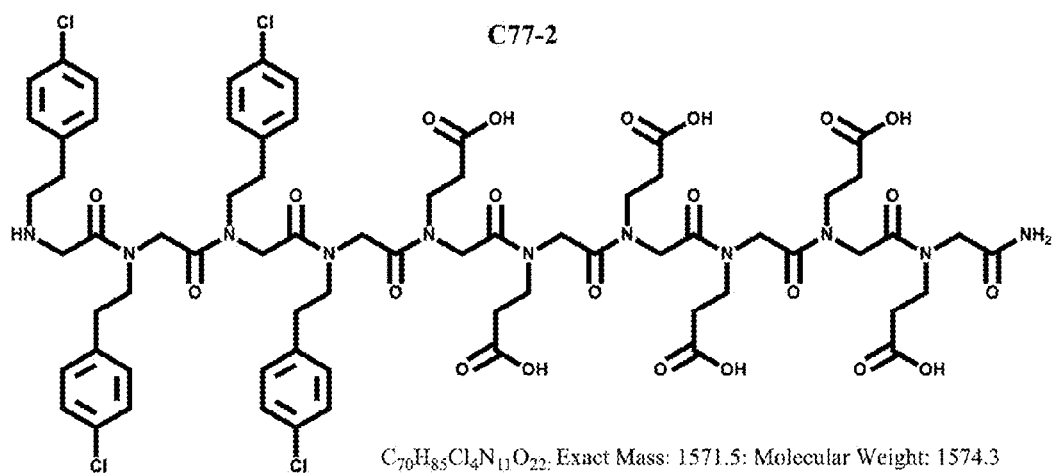
FIG. 8 shows the structure of peptoid C77-2.
Figure 9:
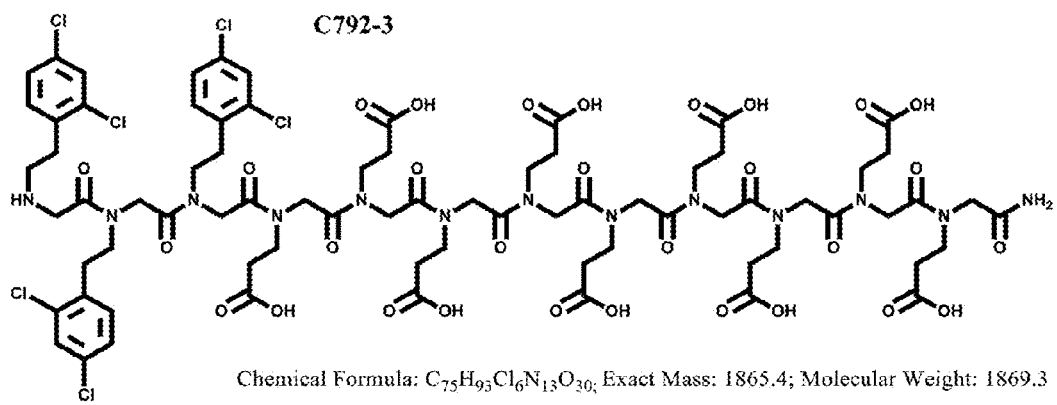
FIG. 9 shows the structure of peptoid C792-3.
Figure 10:
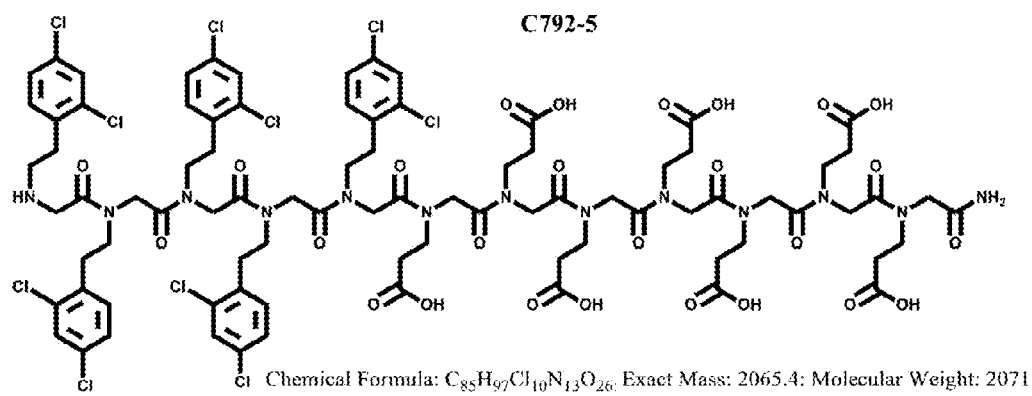
FIG. 10 shows the structure of peptoid C792-5.
Figure 11:
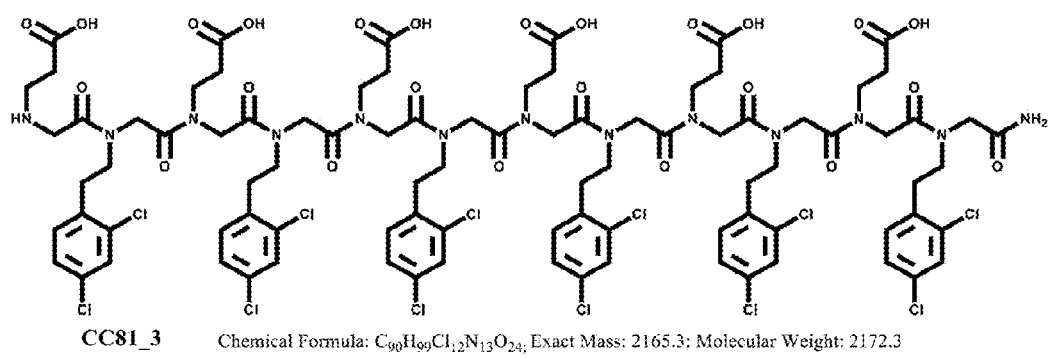
FIG. 11 shows the structure of peptoid CC81-3.
Figure 12:
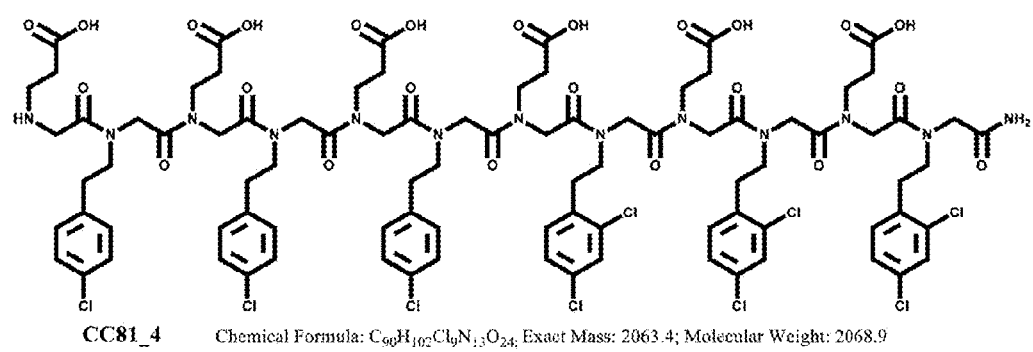
FIG. 12 shows the structure of peptoid CC81-4.
Figure 13:
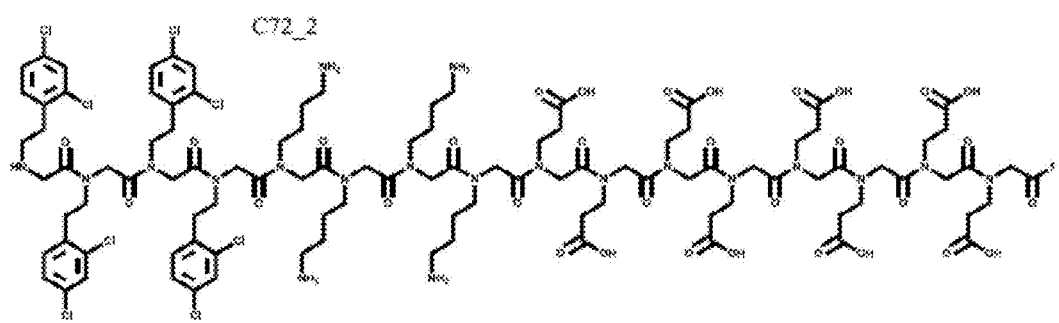
FIG. 13 shows the structures of peptoids C72-2, C27-1, CC77-7, and CC74-2.
Figure 13:
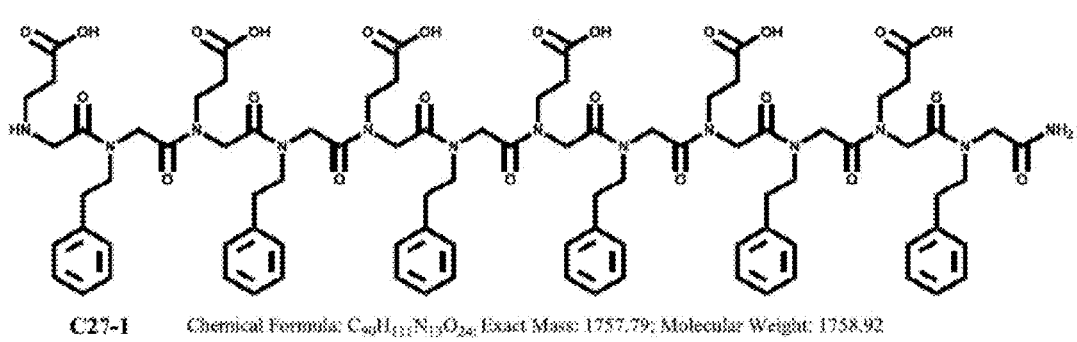
Figure 13:
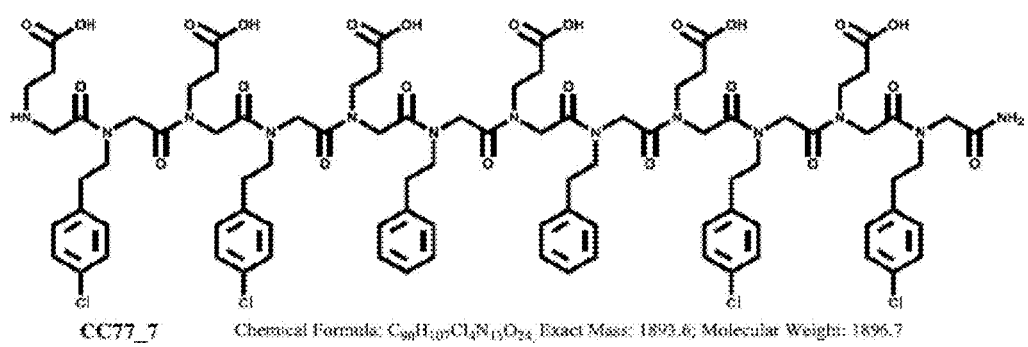
Figure 13:
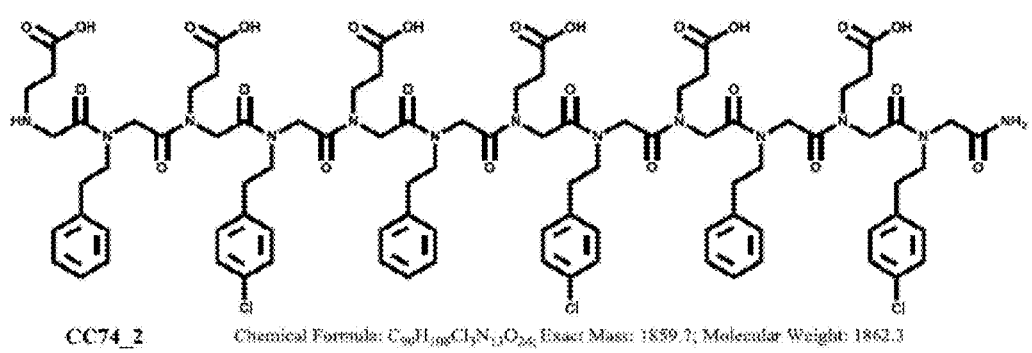
Figure 14:
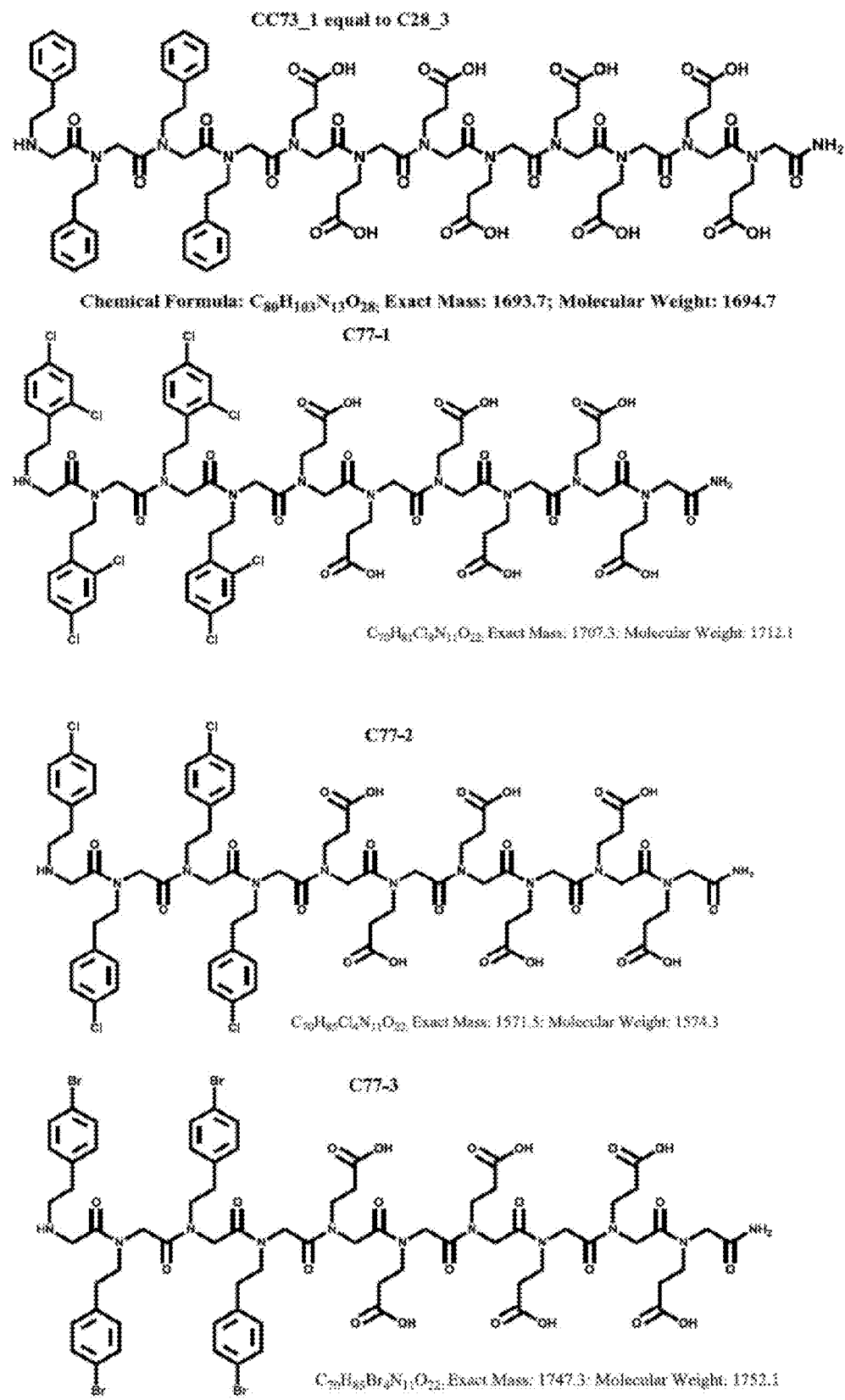
FIG. 14 shows the structures of peptoids CC73-1, C77-1, C77-2, and C77-3.

Peptoid combined PILP approach induce mineralization at intrafibrillar and extrafibrillar compartments of dentinal collagen matrix, as well as peritubular part of dentin tubules so that the remineralized lesion resembles normal dentin. The regrowth of peritubular dentin comprise lamellae of well-crystalline apatite crystals stacking and co-aligned (FIG. 6). In contrast, PILP method (poly-L-Aspartate alone) induces mainly intrafibrillar mineralization in collagen matrix. The length of peptoid pre-incubation promotes the regrowth of peritubular dentin in proportion (FIG. 7, <1-hour and 5-day pre-incubation). Mixing peptoids with poly-L-aspartate, i.e., no pre-incubation, do not produce noticeable peritubular mineralization (FIG. 7).

A peptoid enhance PILP approach promotes mineralization, probably in both intra- and extra-fibrillar compartments in dentin lesions, as indicated by SEM (FIG. 5) and SAXS results.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing an apatite, comprising:
   (a) providing a bio-mimetic polymer capable of catalyzing or mineralizing calcium ions and phosphate ions into the apatite, and
   (b) contacting the bio-mimetic polymer with calcium ions and phosphate ions, such that the apatite is formed; wherein the bio-mimetic polymer is peptoid C792-5.

2. The method of claim 1, wherein the providing step further comprises providing a polyanionic polymer.

* * * * *